United States Patent [19]
Levy et al.

[11] Patent Number: 5,290,274
[45] Date of Patent: Mar. 1, 1994

[54] LASER APPARATUS FOR MEDICAL AND DENTAL TREATMENTS

[75] Inventors: Guy Levy, Tustin; Philippe Levy, San Clemente; James H. Tillotson, Rancho Mirage, all of Calif.

[73] Assignee: Laser Medical Technology, Inc., San Clemente, Calif.

[21] Appl. No.: 899,288

[22] Filed: Jun. 16, 1992

[51] Int. Cl.$^5$ .............................................. A61B 17/38
[52] U.S. Cl. ...................................... 606/13; 606/11; 606/2; 606/3
[58] Field of Search ............................ 606/2, 3, 7–12, 606/14, 15, 16; 128/395–398

[56] References Cited

U.S. PATENT DOCUMENTS

| | | | |
|---|---|---|---|
| 4,418,689 | 12/1983 | Kanazawa | 606/2 X |
| 4,478,217 | 10/1984 | Shimada et al. | 606/13 |
| 4,503,854 | 3/1985 | Jako | 606/11 |
| 4,573,465 | 3/1986 | Sugiyama et al. | 606/11 |
| 5,139,494 | 8/1992 | Freiberg | 606/3 |
| 5,172,264 | 12/1992 | Morrow | 606/11 X |

FOREIGN PATENT DOCUMENTS 9012619 11/1990 PCT Int'l Appl. ............... 606/2

*Primary Examiner*—Peter A. Aschenbrenner
*Attorney, Agent, or Firm*—Spensley Horn Jubas & Lubitz

[57] ABSTRACT

A method and apparatus for performing a medical or dental treatment by: providing radiation at two different wavelengths and at respective power levels such that the radiation at each wavelength is individually capable of cutting a given organic tissue; simultaneously applying the laser radiation at the two different wavelengths to a single body region which is composed of the given tissue; and directing a cooling fluid at the single body fluid region simultaneously with the step of applying radiation.

14 Claims, 1 Drawing Sheet

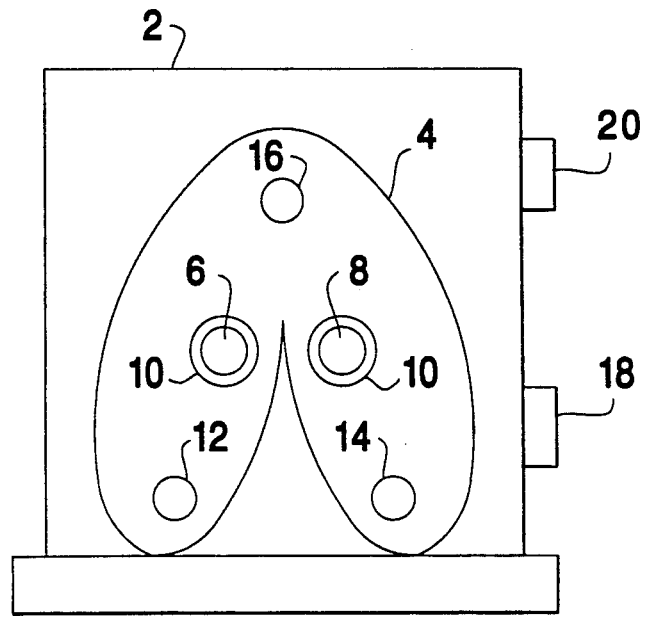
Fig. 1
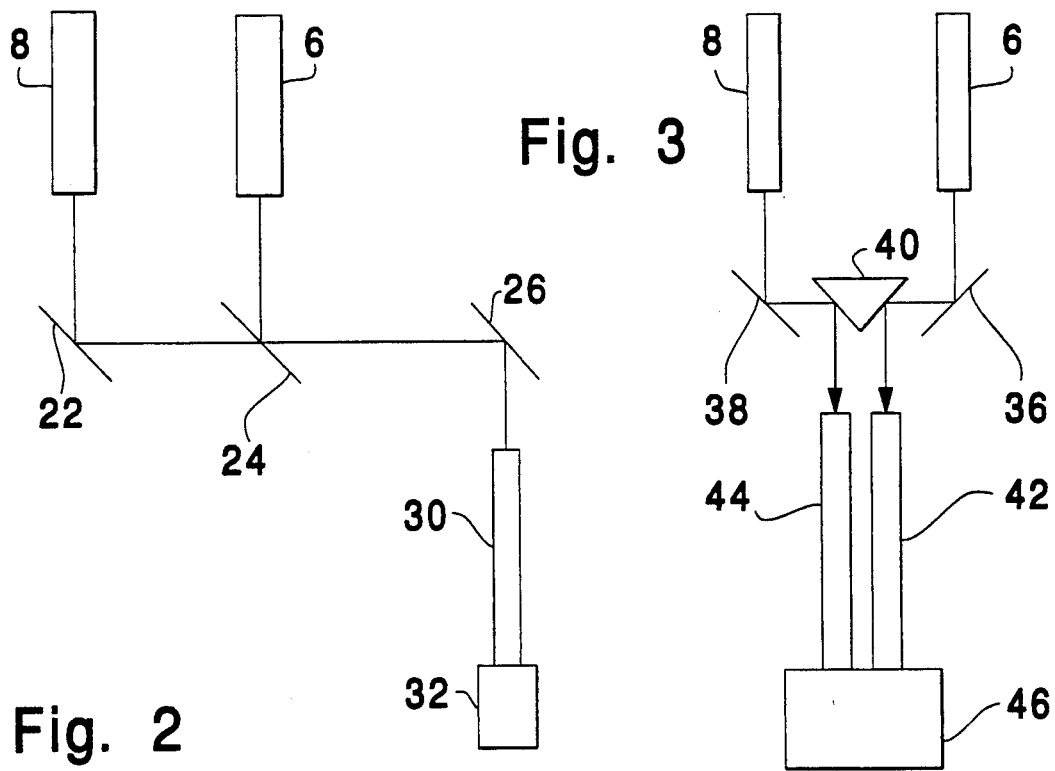
Fig. 2
Fig. 3

LASER APPARATUS FOR MEDICAL AND DENTAL TREATMENTS

BACKGROUND OF THE INVENTION

The present invention relates to apparatus constituting a source of laser radiation for use in medical and dental treatments, and to treatment methods which can be performed with such apparatus.

Laser radiation is currently employed in medicine and dentistry for performing a variety of procedures, including procedures which involve cutting, or vaporizing, soft tissues. Specifically, devices known as laser scalpels or laser knives have found acceptance in place of conventional scalpels.

It is also known that laser radiation can be employed to promote healing, and to effect cauterization, coagulation and sterilization among others.

In addition, considerable research has demonstrated the ability of laser radiation having a suitable wavelength and energy density to cut hard tissues, including bone, enamel, dentin and cementum, as well as demineralized hard tissue such as carious tooth tissue. In dental applications, soft tissue which can be cut includes gum, nerve tissue and pulp. Laser radiation can also be employed to cut tartar, plaque or calculus which forms on tooth surfaces, as well as similar materials which accumulate in body passages, including blood vessels and urinary passages.

The term "cutting" used herein encompasses mechanisms such as vaporization, which may be achieved by photoablation, or photodisruption.

The effect of laser radiation on any particular tissue depends essentially on the wavelength and power level of the radiation and the form in which the radiation is delivered, i.e. continuous-wave (CW) or pulsed. Heretofore, it has been the practice, when seeking to perform a particular procedure, whether clinically or in connection with research, to seek the type of laser whose wavelength will be most effective for that procedure, and to then seek to arrive at optimum values for power level and, if pulsed radiation appears preferable, the optimum values for pulse duration and repetition rate. The energy delivered by each such pulse will be a product of the laser power output and the pulse duration. The energy density with which each pulse is applied to tissue being treated will depend on the diameter of the radiation spot on the tissue and is a significant parameter in determining the effect of such laser radiation.

In procedures of the type described above, the ability to apply the radiation to a desired location is of substantial importance and it is known to be desirable to apply the radiation by means of a handpiece which can be easily directed by the physician or dentist. Since, however, lasers themselves, particularly those which must produce the power levels required by such medical treatments, are relatively bulky devices, a handpiece is usable only if a feasible means exists for conducting laser radiation from the laser itself to the handpiece. Optical fibers represent a logical and attractive solution to this problem. However, radiation produced by many of the lasers which are currently in use cannot be satisfactorily transmitted via optical fibers. This is true, for example, for $CO_2$ laser radiation.

On the other hand, it is known that radiation wavelengths from about $0.5\mu$ at least up to about $3\mu$ can be efficiently transmitted via conventional optical fibers, at least at relatively low power levels.

Laser radiation having a wavelength of less than $3\mu$ includes those produced by the Nd:YAG laser (fundamental wavelength $1.06\mu$) and the Er:YAG laser (fundamental wavelength of $2.94\mu$). Both of these forms of laser radiation are capable of cutting various types of tissue, although each employs a somewhat different mechanism to do so. This difference results in part from the fact that water has a very low coefficient of absorption for radiation at the wavelength of $1.06\mu$ and a relatively high absorption coefficient for radiation at the wavelength of $2.94\mu$.

U.S. Pat. Nos. 4,931,053 and 4,951,663, to L'Esperance, Jr., disclose apparatus including two lasers producing beams which are aligned onto a common output axis. The laser radiation is selected to avoid inducing photocoagulation, photonoptical tissue breakdown, photovaporization, or photoablative decomposition of the affected body tissue or cells.

According to U.S. Pat. No. 4,931,053, the radiation is selected to enhance vascular or like growth beyond what may be achieved by a single laser.

According to U.S. Pat. No. 4,951,663, the laser radiation is selected to provide a biomedical sterilization system which can destroy microorganisms in the dermis as well as in the epidermis.

U.S. Pat. No. 4,925,523, to Braren et al, discloses apparatus in which beams of laser radiation at the wavelengths of 193 nm and 308 nm are aligned on a common output axis and are applied to a workpiece to produce an enhanced ablative effect. The 193 nm radiation excites molecules of the workpiece material to cause some of the molecules to ablate and others to enter the triplet state without ablating. The 308 nm wavelength ablates molecules which have been placed in the triplet state. The 308 nm wavelength can not itself ablate molecules which have not been excited. This patent mentions other wavelength pairs, describes the effect of the radiation on various plastic materials, and hypothesizes that the method can be used to etch organic substrates including tissue, bone and teeth.

U.S. Pat. No. 4,408,602, to Nakajima, discloses a system having two laser cutting sources each of which is effective on different types of tissues, means being provided to switch between sources.

SUMMARY OF THE INVENTION

It is an object of the present invention to improve the treatment which can be performed with laser radiation and increase the variety of treatments which can be performed safely and effectively through the use of laser radiation.

Another object of the invention is to combine the advantages of a plurality of different laser wavelengths, each of which can individually produce a cutting effect, by vaporization, of organic tissue, particularly in a manner which compensates for the shortcomings of one or more of those wavelengths.

Another object of the invention is to achieve a greater degree of control over medical and dental procedures which utilize laser radiation.

The above and other objects are achieved, according to the present invention, by medical treatment apparatus comprising laser means comprising first and second laser radiation sources each for producing laser radiation at a respectively different wavelength capable of cutting organic tissue; laser radiation applying means for directing laser radiation at body tissue to be treated; radiation conducting means including at least one optical fiber connected for conducting laser radiation from the sources to the applying means; and cooling fluid delivery means for directing a cooling fluid at the body tissue at which the laser radiation is directed.

Objects according to the invention are further achieved by a method of performing a medical or dental treatment with the apparatus as defined above, comprising applying radiation from both sources to body tissue so that radiation from both sources acts on the same body tissue region; and directing cooling fluid at the same body tissue region by the cooling fluid delivery means.

Preferably, the laser radiation sources are an Nd:YAG laser and an Er:YAG laser.

BRIEF DESCRIPTION OF THE DRAWING

FIG. 1 is a simplified cross-sectional view showing the main components of a laser unit according to the present invention.

FIGS. 2 and 3 are simplified pictorial views illustrating two arrangements for directing laser radiation from the laser device of FIG. 1.

DESCRIPTION OF THE PREFERRED EMBODIMENTS

The laser device according to a preferred embodiment of the present invention is a combined Nd:YAG and Er:YAG laser. Hereinafter, for the sake of brevity, these will be referred to as a "Nd laser" and an "Er laser".

The apparatus illustrated in FIG. 1 includes a housing 2 containing an optical reflector 4 which encloses a laser formed by an Nd doped YAG laser rod 6 and a laser formed by an Er doped YAG laser rod 8. Each of rods 6 and 8 is surrounded by a suitable optical filter 10.

Within the region enclosed by reflector 4 there are also disposed three gas filled flash lamps 12, 14 and 16.

Lamps 12, 14 and 16 provide light radiation which will have the effect of optically pumping the Nd and Er lasers.

In the embodiment illustrated in FIG. 1, reflector 4 is formed to approximate two partially overlapping ellipses, reflector 4 being shaped to concentrate the light produced by lamp 12 substantially completely within rod 6, and to concentrate the light produced by lamp 14 substantially completely within rod 8, while the light produced by lamp 16 is distributed substantially equally between rods 6 and 8.

The interior of housing 2 is preferably water cooled, circulation of water between the interior of housing 2 and a heat sink being effected via coupling unit 18. Electrical power for lamps 12, 14 and 16 is delivered into housing 2 via connector unit 20.

With suitable reflectors (not shown) disposed at the ends of rods 6 and 8, the application of light from lamps 12 and 14 and/or lamp 16 will cause laser radiation to be generated within rods 6 and 8 and to be emitted via a transparent portion of the reflector at one end of each rod.

The radiation power produced by each rod 6, 8 will depend on the intensity and wavelength of the light supplied to each rod by lamps 12, 14 and 16. Therefore, the relation between the power levels of the radiation emanating from the two rods 6 and 8 can be adjusted by varying the voltage applied to each of lamps 12, 14 and 16. In this case, variation of the voltage across lamp 16 will have a proportional effect on the output power from both rods 6, 8.

In addition, laser radiation pulses can be produced by operating respective ones of lamps 12 and 14 in a pulsed manner, i.e. the duration and repetition rate of the pulses produced by each rod 6, 8, will correspond to the duration and repetition rate, respectively, of the operating voltage pulses applied to the respective one of lamps 12 and 14. Control of the operation of lamps 12 and 14 can be effected by a microprocessor controlled power supply system.

According to a particular feature of the invention, lamps 12, 14 and 16 may be filled with a special mixture of krypton and xenon to provide optimum pumping of the laser media within rods 6 and 8. This mixture can vary over a wide range. An improvement relative to use of only one ingredient or the other will become apparent if each ingredient is present in the mixture in a concentration greater than 2%, by weight.

The power level of the laser radiation emitted from each laser rod 6, 8 can be individually adjusted, as can the pulse timing, duration and repetition rate when the Nd and/or Er laser radiation is in the form of a succession of pulses, by applying individually controlled operating voltages to each of lamps 12 and 14 and operating lamp 16 at a level such that its output can not, by itself, cause rod 6 or 8 to emit radiation.

Two possible arrangements for conducting this radiation to a handpiece are shown in FIGS. 2 and 3.

In the embodiment shown in FIG. 2, radiation from Er laser 8 is reflected by a first mirror 22, passes through a second mirror 24 and is reflected by a third mirror 26 onto the input end of a transmission fiber 30. Radiation from laser 6 is reflected by second mirror 24 and is reflected by third mirror 2 onto the input end of fiber 30. According to principles known in the art, mirrors 22, 24 and 26 may be dichroic mirrors each constructed to reflect a selected radiation wavelength and/or transmit a selected wavelength. Specifically, mirror 22 is constructed to reflect, to the greatest extent possible, Er radiation at a wavelength of 2.94 microns, mirror 24 is constructed to be highly transmissive with respect to Er radiation while having the highest reflectivity possible with respect to Nd radiation at a wavelength of 1.06 microns and mirror 26 is constructed to have the highest reflectance possible with respect to both 1.06 and 2.94 microns.

Fiber 30 extends from the region adjacent mirror 26 to a suitable handpiece 32.

In the embodiment shown in FIG. 3, the output radiation from rods 6 and 8 are reflected by respective mirrors 36 and 38 onto a reflecting device 40, which may be a non-linear open crystal or di-cell laser combiner, which directs the radiation from each rod into a respective one of two parallel optical fibers 42 and 44 which extend to a handpiece 46.

The use of two fibers allows a higher total power level to be delivered to handpiece 46 while allowing fibers 42 and 44 to be made sufficiently thin to have a high degree of flexibility. Handpiece 46 may contain conventional radiation combining elements for directing radiation from both sources along a common axis.

The apparatus illustrated in the drawing and described above can be employed for delivering Nd laser radiation, Er laser radiation, or a combination of those two forms of radiation with any desired combination of power levels, pulse durations and pulse repetition rates. As a result, a single apparatus can be employed to perform a wide variety of procedures and can go beyond the capabilities of any prior art apparatus by performing procedures with a combination of the two forms of radiation.

Several examples of the benefits which can be achieved through use of apparatus according to the invention will be described below, with reference to the above-describe specific embodiment which includes an Nd laser radiation source and an Er laser radiation source.

Prior research has demonstrated that Nd laser radiation, when employed with a cooling system, can be effective on both hard and soft tissues. In particular, hard tissue can be cut, or vaporized, with radiation at the fundamental frequency of 1.06 microns, while soft tissue can be cut more effectively with frequency doubled radiation at a wavelength of 0.532 micron. Both wavelengths are essentially not absorbed by water and act directly on non-aqueous tissue components. The delivery of an aqueous cooling spray at the area being irradiated withdraws the heat generated by the laser radiation and serves to substantially minimize the damage envelope around the tissue region which has been cut, or vaporized.

The Er laser, which has appeared more recently in the field, produces radiation at a wavelength which is highly absorbed by water and very highly absorbed by hydroxyapatite. Therefore, the Er laser can efficiently cut both soft tissue and hard tissue. When such a laser is employed without simultaneously cooling the irradiated tissue, the histological results are not good in that healing occurs relatively slowly due to the creation of a large damage envelope and some carbonization around the region which has been vaporized or cut.

The Er laser appears to be capable of cutting or vaporizing tooth enamel with a high efficiency because this tissue has a small amount of water, between 2 and 3%, so that the radiation energy is efficiently absorbed by the hydroxyapatite. In fact, a plasma can be obtained with photodisruption with pulses of radiation at a low average power level of between and 3 and 6 watts. Pulse duration may be of the order of 100 $\mu$sec to 1 ms. The pulse repetition rate may be of the order of 30–50 Hz and the radiation may be focused, at the surface to be cut, to a spot size of 150–600$\mu$. However, other values for these parameters may prove suitable.

However, radiation from the Er laser has been found to cause an undesired side effect on enamel, involving the creation of cracks when radiation is applied without the simultaneous application of a cooling liquid. It has been demonstrated that when cooling is produced by the application of a stream or spray of cooling liquid, then the occurrence of cracks is prevented. However, since Er laser radiation is absorbed to a substantial extent by water, the efficiency of this laser in the presence of a cooling stream of spray is considerably reduced, which means that the energy of the radiation pulses must be increased in order to effect efficient cutting.

The Er laser is also capable of cutting dentin and bone, but does so with less efficiency than the Nd laser, and has a tendency to produce carbonization due to the fact that these tissues have a large amount of water, between 20 and 30%, which will absorb, and be heated by, the Er laser radiation energy. Because this radiation is absorbed to a high degree by water, the laser pulses must be at a high energy level. As a result, thermal effects become more significant, resulting in the creation of a relatively large damage envelope around the cut tissue, which slows the healing process.

In addition, it is more difficult to conduct Er radiation via conventional optical fibers. Specifically, because of the longer wavelength of Er laser radiation, the Er laser radiation conducted by such optical fibers cannot have an average power level of more than about 3 or 4 watts.

On the other hand, Nd laser radiation is absorbed to a significant degree by hydroxyapatite and is hardly absorbed at all by water, i.e. water is transparent to this radiation wavelength. Therefore, Nd laser radiation is very efficient for cutting both soft and hard tissues. Moreover, Nd laser radiation can be easily delivered at high power levels via conventional silica optical fibers, even fibers having diameters of the order of 100 to 150 microns, which are suitable for use in widening tooth canals.

On hard tissue, Nd laser radiation can effectively cut bone, dentin, cementum or enamel and photodisruption can be achieved even at low average power levels of the order of 6 watts and even with pulses of long duration because the energy density supplied to the tissue can be made sufficiently high to produce a photodisruption effect that creates an acoustic breakdown which avoids the direct transmission of heat to the tissue. This photodisruption effect, when combined with the supply of a stream of cooling fluid, preferably a spray composed of air and water, results in a very small damage envelope and allows healing to occur rapidly. The damage envelope is the region which borders the void or recess created by the vaporization of tissue and in which damage to the tissue as a result of the laser radiation can be observed. Moreover, the efficiency with which bone and dentin can be cut with Nd laser radiation is very good. However, it has been found that with respect to enamel, a part of the radiation energy is reflected and scattered by the enamel crystals.

By combining Er laser radiation and Nd laser radiation for cutting procedures, improved results are achieved. When the apparatus according to the invention is used to cut enamel in the presence of a cooling water spray, the cutting efficiency of the Er laser radiation will be reduced but the coupling between the Er and Nd radiations will enhance the cutting efficiency of the Nd radiation because the photodisruption produced by Er radiation, even at low power levels of 3–4 watts, will increase the absorption of the Nd radiation by the enamel which has been transformed by the photodisruption. Effectively, such photodisruption will modify or destroy the crystalline structure of the affected enamel. As a result, scattering of radiation at the wavelength of 1.06$\mu$, which would be produced by the crystalline structure, is substantially reduced so that absorption of radiation at 1.06$\mu$ is substantially increased. Thus, cutting efficiency is enhanced without requiring that the Er radiation be at a high power level. This means that both types of radiation can be conducted by a conventional silica fiber doped with fluoride and having a diameter of 600$\mu$ or less without burning or otherwise damaging the fiber.

In addition, use can be made of disposable fibers and fibers having a tapered distal end, the fibers tapering, for example, from a diameter of 600$\mu$ to a diameter of 100 to 200$\mu$.

As a result of the effect described above, combined radiation according to the invention can be efficiently cut enamel, dentin, cementum and bone.

In the case of soft tissue, Er laser radiation will produce a shallow, or superficial, cut and Nd laser radiation will deepen the cut because it is absorbed only to a small degree by water. Satisfactory results can be achieved with Nd laser radiation at $1.06\mu$, so embodiments of the invention may be constructed without the frequency doubling elements required to give the Nd laser radiation a wavelength of $0.532\mu$.

According to preferred embodiments of the invention, the Er laser may produce an output at an average power level of 3-6 watts and the Nd laser may produce an output at an average power level of 1-15 watts. For cutting bone, the Nd average power output can be as high as 40 watts.

The pulse repetition rate could, for example, be between 100 $\mu$s and several ms, preferably 800 $\mu$s, for each of lasers 6 and 8. The radiation spot size may be $150$-$600\mu$.

The pulse repetition rate for each wavelength is preferably 50 Hz.

The types of soft tissue which may be cut include gum, pulp and root material, and the soft tissues encountered in general surgery.

The types of hard tissue which may be cut include healthy or decayed enamel, dentin, cementum and bone in dentistry, for example to perform apicoectomies, as well as in traumatology, orthopedics and veterinary medicine.

In endodontics, radiation according to the invention can be delivered via a thin optical fiber to provide access to the pulp chamber, to remove pulp therefrom, to prepare a root canal, sterilize the canal wall and to clean and shape the canal.

At low energy levels, the laser radiation can be used to desensitize tooth tissue, particularly the root structure.

The radiation can also be used in periodontics to sterilize a pocket, cut gingivae and remove calculus and tartar.

The radiation can be used for welding or for bonding a preparation containing hydroxyapatite to tooth or bone material.

When such combined radiation is applied to tissue, it remains essential that a stream or spray containing a cooling liquid, preferably water, be applied simultaneously to the irradiated region.

A combined beam of Er and Nd radiation can also enhance the cutting, by vaporization, of inorganic materials, such as steel. In this case, photodisruption created by the Nd laser radiation is enhanced by the Er laser radiation.

Apparatus according to the invention can also be employed to achieve hemostasis, or control of bleeding, in wounds and incisions. This procedure requires energy density levels lower than those required for cutting and can therefore be performed with a beam formed to have a larger spot size than that required for cutting. The Er laser radiation will effect superficial hemostasis and the Nd laser radiation at $1.06\mu$ will effect deeper hemostasis. If Nd laser radiation at $0.532\mu$ were available, it would effect a shallower homeostasis; this wavelength is well absorbed by red pigment such as that in hemoglobin. While, as noted above, preferred embodiments of the invention include an Er laser and an Nd laser, other lasers capable of a type of synergism similar to those described above may be employed. To cite one example, the Nd laser could be replaced by an alexandrite laser which produces radiation at a wavelength of $0.730\mu$ to $0.790\mu$. Radiation in this wavelength range is substantially absorbed by hemoglobin and hydroxyapatite, is slightly absorbed by water and is scattered by enamel. For soft tissue treatments, cutting and hemostasis, its effect is between those produced by Nd laser radiation at $0.532\mu$ and $1.06\mu$.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. Medical treatment apparatus comprising:
   laser means comprising
      first and second laser radiation sources each for producing laser radiation at a respectively different wavelength and power level capable of cutting a given organic tissue, each of said radiation sources comprising a respective laser radiation emitting body having a laser medium which determines the respective laser radiation wavelength, and
      optical pumping means disposed for supplying pumping energy to said bodies for causing said bodies to produce laser radiation, said optical pumping means comprising a first lamp optically coupled exclusively to one of said bodies, a second lamp optically coupled exclusively to the other of said bodies, and a third lamp optically coupled to both of said bodies;
   laser radiation applying means for directing laser radiation at body tissue to be treated;
   radiation conducting means including at least one optical fiber connected for conducting laser radiation from said sources to said applying means; and
   cooling fluid delivery means for directing a cooling fluid containing water at the body tissue at which the laser radiation is directed.

2. Apparatus as defined in claim 1 wherein said laser means further comprise laser beam control means for placing the radiation produced by each of said sources in the form of a succession of pulses at a selected pulse repetition rate, each pulse having a selected duration.

3. Apparatus as defined in claim 1 wherein said radiation conducting means comprise: an optical fiber extending between said laser means and said radiation applying means; and radiation combining means disposed between said radiation sources and said fiber for combining radiation from the two sources and introducing the combined radiation into said fiber.

4. Apparatus as defined in claim 3 wherein said radiation source produces radiation at a wavelength in the vicinity of $0.7\mu$ to $1\mu$ and said second radiation source produces radiation at a wavelength in the vicinity of $3\mu$.

5. Apparatus as defined in claim 1 wherein said radiation conducting means comprise two optical fibers each extending between said laser means and said radiation applying means; and radiation directing means disposed between said radiation sources and said fiber for directing radiation from each source into a respective fiber.

6. Apparatus as defined in claim 5 wherein said first radiation source produces radiation at a wavelength in the vicinity of 0.7μ to 1μ and said second radiation source produces radiation at a wavelength in the vicinity of 3μ.

7. Apparatus as defined in claim 1 wherein said radiation conducting means comprise: an optical fiber extending between said laser means and said radiation applying means; and radiation combining means disposed between said radiation sources and said fiber for combining radiation from the two sources and introducing the combined radiation into said fiber.

8. Apparatus as defined in claim 7 wherein said first radiation source produces radiation at a wavelength in the vicinity of 0.7μ to 1μ and said second radiation source produces radiation at a wavelength in the vicinity of 3μ.

9. Apparatus as defined in claim 1 wherein said radiation conducting means comprise two optical fibers each extending between said laser means and said radiation applying means; and radiation directing means disposed between said radiation sources and said fiber for directing radiation from each source into a respective fiber.

10. Apparatus as defined in claim 9 wherein said first radiation source produces radiation at a wavelength in the vicinity of 0.7μ to 1μ and said second radiation source produces radiation at a wavelength in the vicinity of 3μ.

11. Apparatus as defined in claim 1 wherein said cooling fluid delivery means are for directing a mixture of air and water in the form of a spray at the body tissue.

12. A method of performing a medical or dental treatment with the apparatus as defined in claim 1, comprising:
  applying radiation from both sources to body tissue so that radiation from both sources acts on the same body tissue region; and
  directing the cooling fluid at the same body tissue region by the cooling fluid delivery means.

13. The method as defined in claim 12 further comprising individually adjusting the power level of the radiation from each source.

14. Apparatus as defined claim 12 wherein said step of directing comprises directing a spray composed of a mixture of air and water.

* * * * *